United States Patent
Risbud Bartl et al.

(10) Patent No.: US 10,290,387 B2
(45) Date of Patent: May 14, 2019

(54) MODIFICATION OF COLLOIDAL NANOCRYSTALS

(71) Applicant: University of Utah Research Foundation

(72) Inventors: Michael Hans Risbud Bartl, Cupertino, CA (US); Jacqueline T. Siy, Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 198 days.

(21) Appl. No.: 14/811,715

(22) Filed: Jul. 28, 2015

(65) Prior Publication Data
US 2015/0332801 A1    Nov. 19, 2015

Related U.S. Application Data

(63) Continuation-in-part of application No. 13/142,191, filed as application No. PCT/US2010/021461 on Jan. 20, 2010, now abandoned.
(Continued)

(51) Int. Cl.
*H01B 1/12* (2006.01)
*C07F 3/00* (2006.01)
(Continued)

(52) U.S. Cl.
CPC ............. *H01B 1/12* (2013.01); *C07F 3/00* (2013.01); *C07F 7/24* (2013.01); *C09K 11/88* (2013.01);
(Continued)

(58) Field of Classification Search
CPC ........ H01B 1/12; C09K 11/883; C09K 11/88; C09K 2211/10; C07F 3/00; C07F 7/24
See application file for complete search history.

(56) References Cited

U.S. PATENT DOCUMENTS 6,274,323 B1 * 8/2001 Bruchez ............... B82Y 15/00
                                                    435/6.11
6,645,444 B2   11/2003 Goldstein
(Continued)

FOREIGN PATENT DOCUMENTS

JP    2004510678    4/2004
JP    2004524381    8/2004
(Continued)

OTHER PUBLICATIONS

Peng, Z., et al, Mechanism of the Shape Evolution of CdSe Nanocrystals, J. Am. Chem. Soc., 2001, 123, 1389-95.*
(Continued)

*Primary Examiner* — Mark Kopec
*Assistant Examiner* — Jaison P Thomas
(74) *Attorney, Agent, or Firm* — Workman Nydegger (57) ABSTRACT

Methods for precise and predictable modification of previously synthesized nanocrystals. The methods rely on the solubility behavior of crystalline materials to provide for controlled reversal of the nanocrystal growth process (i.e., dissolution). A method for post-synthesis modification of colloidal nanocrystals includes (1) providing a first nanocrystal having a first size and a first shape, (2) forming a reaction mixture that includes the nanocrystal, at least one ligand capable of binding to at least one component of the nanocrystal, at least one solvent, and an inert gas atmosphere, and (3) modifying the size and/or shape of the nanocrystal in the reaction mixture for a period of time at a temperature in a range from about 100° C. to about 240° C. so as to produce at least a second nanocrystal having a second size and/or a second shape.

20 Claims, 3 Drawing Sheets

Related U.S. Application Data (60) Provisional application No. 61/145,925, filed on Jan. 20, 2009.

(51) Int. Cl.
   *C07F 7/24* (2006.01)
   *C09K 11/88* (2006.01)

(52) U.S. Cl.
   CPC ........ *C09K 11/883* (2013.01); *C09K 2211/10* (2013.01)

(56) References Cited

U.S. PATENT DOCUMENTS

| | | | |
|---|---|---|---|
| 6,872,249 B2 * | 3/2005 | Peng | B82Y 30/00 117/68 |
| 7,178,747 B2 | 2/2007 | Yadav | |
| 2004/0247503 A1 | 12/2004 | Hyeon | |
| 2005/0129947 A1 | 6/2005 | Peng | |
| 2006/0211152 A1 | 9/2006 | Peng et al. | |
| 2006/0216759 A1 | 9/2006 | Naasani | |
| 2007/0264834 A1 * | 11/2007 | Strouse | B01J 13/00 438/708 |
| 2008/0057311 A1 | 3/2008 | Hollingsworth et al. | |
| 2011/0140046 A1 | 6/2011 | Yu et al. | |

FOREIGN PATENT DOCUMENTS

| | | |
|---|---|---|
| JP | 2005536634 | 12/2005 |
| JP | 2005536634 A | 12/2005 |
| JP | 2006143526 | 6/2006 |
| JP | 2006143526 A | 6/2006 |
| JP | 2007181810 | 7/2007 |
| JP | 2007181810 A | 7/2007 |
| JP | 2010522133 | 7/2010 |
| JP | 2010522133 A | 7/2010 |
| JP | 2012515707 | 7/2012 |
| JP | 2012515707 A | 7/2012 |
| WO | 2007086267 | 8/2007 |
| WO | 2008116661 | 10/2008 |
| WO | 2010085463 | 7/2010 |

OTHER PUBLICATIONS

Alivisatos et al., "Perspectives on the Physical Chemistry of Semiconductor Nanocrystals," *The Journal of Physical Chemistry*, 100 13226 (1996).
Alivisatos et al., "Quantum Dots as Cellular Probes," Annual Rev. Biomed. Eng. 7:55-76 (2005).
Alivisatos et al., "Semiconductor Clusters, Nanocrystals, and Quantum Dots," *Science*, 271, 933 (1996).
Baxter et al. "Synthesis and Characterization of ZnO Nanowires and Their Integration into Dye-Sensitized Solar Cells," *Nanotechnology* 17: S304-S312 (2006).
Biju et al. "Semiconductor Quantum Dots and Metal Nanoparticles: Syntheses, Optical Properties, and Biological Applications," *Analytical and Bioanalytical Chemistry*, 391: 2469 (2008).
European Search Report EP10733794 dated May 26, 2014.
Han, W., et al., "Synthesis and Shape-Tailoring of Copper Sulfide/Indium Sulfide-Based Nanocrystals," *Journal of the American Chemical Society*, vol. 130 (2008) pp. 13152-13161.
Hayden et al. "Nanoscale Avalanche Photodiodes for Highly Sensitive and Spatially Resolved Photon Detection," *Nature Materials*, vol. 5, 352 (2006).
International Search Report and Written Opinion for PCT/US2010/021461 dated Mar. 10, 2010.
Law et al. "Nanowire Dye-Sensitized Solar Cells" *Nature Materials*, vol. 4, 455 (2005).
Li et al. "Amine-Assisted Facetted Etching of CdSe Nanocrystals," *Journal of the American Chemical Society*, 127 2524 (2005).
Marzan et al. "New Aspects of Nanocrystal Research," *MRS Bull* 26, 981-984 (2001).
Murray et al. "Monodisperse 3d Transition-Metal (Co, Ni, Fe) Nanoparticles and Their Assembly into Nanoparticle Superlattices," MRS Bull 26 985 (2001).
Murray et at. "Synthesis Characterization of Monodisperse Nanocrystals and Close-Packed Nanocrystal Assemblies," *Annual Review of Materials Science*, 30:545-610 (2000).
Murray et al., "Synthesis and Characterization of Monodisperse CdE (E=Sulfer, Selenium, Tellurium) Semiconductor Nanocryallites," *Journal of the American Chemical Society*, 115 8706 (1993).
Peng et al., Formation of High-Quality CdTE, CdSe, and CdS Nanocrystals Using CdO as Precursor, *Journal of the American Chemical Society*. 123 183 (2001).
Peng et al., "Nearly Monodisperse and Shape-Controlled CdSe Nanocrystals via Alternative Routes: Nucleation and Growth," *Journal of the American Chemical Society*. vol. 124, 3343 (2002).
Peng et al., "Shape Control of CdSe Nanocrystals," *Nature*, 404, Mar. 2000, p. 59-61.
Raffaelle, et al., "Quantum Dot Solar Cells," Progress in Photovoltaics: Research and Applications 10, 433 (2002).
Reboud et al. "Spontaneous Emission Control of Colloidal Nanocrystals Using Nanoimprinted Photonic Crystals," *Applied Physics Letters* 90 011115 (2007).
Siy, Jacqueline T. et al.; "Effect of Ligand Exchange on the Stability and Optical Properties of CdSe Quantum Dots," *Materials Research Society Symposium Proceedings* vol. 1056 (2008).
Sugiyama, M., et al., "Size and Shape Transformation of TiO2 Nanoparticles by Irradiation of 308-nm Laser Beam," *Japanese Journal of Applied Physics*, vol. 41 (2002) pp. 4666-4674.
Yu et al. "Experimental Determination of the Extinction Coefficient of CdTe, CdSe, and CdS Nanocrystals," *Chemistry of Materials* 15 2854 (2003).
U.S. Appl. No. 13/142,191, dated Dec. 31, 2012, Office Action.
U.S. Appl. No. 13/142,191, dated Jun. 17, 2013, Office Action.
U.S. Appl. No. 13/142,191, dated Jan. 8, 2014, Final Office Action.
U.S. Appl. No. 13/142,191, dated Jul. 30, 2014, Office Action.
U.S. Appl. No. 13/142,191, dated Jan. 29, 2015, Final Office Action.
European Examination Report for EP10733794.1 dated Mar. 27, 2018.

* cited by examiner

MODIFICATION OF COLLOIDAL NANOCRYSTALS

CROSS-REFERENCE TO RELATED APPLICATIONS

This application is a Continuation in Part of U.S. patent application Ser. No. 13/142,191 filed Dec. 7, 2011. U.S. patent application Ser. No. 13/142,191 claims the benefit of and priority to Patent Cooperation Treaty Application No. PCT/US2010/021461 filed Jan. 20, 2010, entitled "POST-SYNTHESIS MODIFICATION OF COLLOIDAL NANOCRYSTALS" which claims priority to U.S. Provisional Patent Application Ser. No. 61/145,925 entitled "METHOD FOR THE POST-SYNTHESIS SHAPE MODIFICATION OF COLLOIDAL NANOCRYSTALS IN SOLUTION" filed 20 Jan. 2009. The entireties of the above listed applications are incorporated herein by reference.

GOVERNMENT LICENSE RIGHTS

This invention was made with government support under grant number ECS0609244 awarded by National Science Foundation. The government has certain rights in the invention.

BACKGROUND

1. The Field of the Invention

The present invention relates to nanocrystals and methods for their fabrication. In particular, the present invention relates to methods for post-synthesis shape and/or size modification of colloidal nanocrystals.

2. The Relevant Technology

Nanocrystals are small crystallites of semiconductors or metals with various shapes (dots, rods, fibers, tetrapods and other geometries) and sizes ranging from 1 to 100 nm. For example, a so-called quantum dot is a semiconductor whose excitons are confined in all three spatial dimensions. The most striking feature of semiconductor and metallic nanocrystals is that, in contrast to bulk material, their electronic and optical properties are dependent on particle size and shape and therefore can be continuously controlled over a large range. These unique features make nanocrystals important candidates for advanced applications in areas as diverse as nano-electronics, nano-photonics, solid-state lightning, energy conversion and storage, and health science. For example, nanocrystals are considered key components for next-generation single-photon generation and detection, encryption, micro-lasing and solar energy conversion. In addition, nanocrystals are intensively studied in biological labeling and imaging as well as for targeted drug delivery. For example, nanocrystals are considered to be superior for use as dyes in biological labeling and imaging when compared to conventional molecular dyes because nanocrystal dyes are brighter and they are not generally subject to photo-bleaching.

This wide range of potential applications has sparked research into the development of robust and universal synthesis routes for the fabrication of nanocrystals with adjustable sizes and shapes. Outstanding in these efforts is the seminal work of Murray, Norris and Bawendi in 1993, who reported a relatively simple and robust solution-based synthesis route for the preparation of nearly monodisperse semiconducting cadmium chalcogenide (i.e., CdS, CdSe and CdTe) semiconductor nanocrystal quantum dots. Their technique uses colloidal crystal-nucleation and growth chemistry at a temperature in range of about 200° C. to about 350° C. in the presence of a long alkyl-chain surfactant/solvent system. Example solvents include long-chain alkylphosphines, long-chain alkylphosphine oxides, and long-chain alkenes. However, the solvent/surfactant system used in high-temperature synthesis methods is generally quite expensive and the solvent/surfactant system is generally not reusable from reaction to reaction.

Following the Bawendi Group's discovery, widespread research has been devoted to the synthesis of various types of nanocrystalline materials. While slight modifications of the original Bawendi method in terms of organometallic precursor species and reaction and crystallizations conditions (concentration of reaction components, solvents, growth time, etc.) have resulted in the development of a wealth of nanocrystals with different compositions, sizes, and shapes, it is interesting to note that the typical synthesis conditions are all based on the original high-temperature (e.g., 200-350° C. for cadmium chalcogenide nanocrystals) crystallite nucleation and growth route.

Following on the work of Bawendi and others, widespread research has also been devoted to developing synthesis methods for nanocrystals having different shapes. Currently nanocrystals with shapes other than near-spherical such as rods, fibers, tetrapods and other geometries are formed either during typical colloidal organometallic chemistry-based synthesis of high-quality nanocrystals or by etching methods of synthesized nanocrystals. In the first method the reaction conditions are adjusted so that nanocrystal growth in one or more dimensions is favorable. While this leads to non-spherical shapes, the elongated shapes in one or more directions leads to the partial loss of the quantum confinement and therefore excitons are no longer three-dimensionally confined. The second method uses acid or base etching to modify the shape of synthesized near-spherical nanocrystals. While three-dimensional quantum confinement is retained in this technique, these processes in general require aqueous acid and/or base environments and therefore require several synthesis and post-synthesis steps to retain nanocrystal quality.

SUMMARY

The present disclosure describes methods in which the shape and/or size of previously synthesized colloidal nanocrystals can be modified. The process relies on controlled reversal of the nanocrystal growth process via competing thermodynamic and kinetic processes, allowing one to predictably control the degree of nanocrystal shape and size-modification. The process enables fabrication of shape-modified nanocrystals with sizes and shapes in the quantum confinement regime, resulting in the three-dimensional confinement of created excitons within the nanocrystals. The nanocrystals therefore possess size- and shape-dependent electronic and optical properties, which makes them interesting candidates for applications in areas as diverse as electronics and photonics, solid-state lightning, energy, and health science. Furthermore, since the methods disclosed herein include a simple one-step process at modest temperatures, high-throughput fabrication and integration into conventional commercial fabrication facilities should readily be possible.

In a first embodiment, a method for nanocrystal modification is disclosed. The method may include steps of (1) providing a first nanocrystal having a first size and a first shape, (2) forming a reaction mixture that includes the nanocrystal, at least one ligand capable of binding to at least one component of the nanocrystal, at least one solvent, and an inert gas atmosphere, and (3) modifying the size and/or shape of the nanocrystal in the reaction mixture for a period of time of at least about 1 minute at a temperature in a range from about room-temperature (i.e., about 15-20° C.) to about 240° C. so as to produce at least a second nanocrystal having a second size and/or a second shape.

In a second embodiment, another method for size and/or shape modification of colloidal nanocrystals is disclosed. The method may include steps including (1) providing colloidal nanocrystals having a first size and a first shape, (2) modifying the size and/or shape of the nanocrystals in a reaction mixture under an inert-gas atmosphere at a temperature in a range from about room-temperature to about 240° C., wherein the reaction mixture includes the nanocrystals, at least one solvent, and at least one ligand capable of binding to at least one component of the nanocrystal, (3) monitoring the modification of the nanocrystals in the reaction mixture using at least one of UV-vis absorption spectroscopy, photoluminescence emission spectroscopy, and/or transmission electron microscopy, and (4) stopping the reaction and purifying the nanocrystals from the reaction mixture when the nanocrystals achieve a selected second size and/or a second shape.

In a third embodiment, yet another method for post-synthesis modification of colloidal nanocrystals is disclosed. The method includes steps including (1) providing a plurality of nanocrystals having a first size and a first shape, (2) forming a reaction mixture that includes the plurality of nanocrystals, at least one inert solvent, and at least one ligand capable of binding to at least one component of the nanocrystal, wherein the nanocrystals and the ligand are added in a molar ratio that ranges from about 1:1 to about $1:1 \cdot 10^{10}$, (3) conditioning the reaction mixture by first stirring under vacuum at ambient temperature and second by stirring under a vacuum at a temperature in a range from about 50° C. to about 100° C., (4) adding an inert-gas to the reaction mixture and heating the reaction mixture to a temperature in a range from about 100° C. to about 300° C., (5) modifying the size and/or shape of the nanocrystals by selectively dissolving the nanocrystals so as to have a second size and shape, wherein the selective dissolving includes maintaining the temperature, stirring, and the inert gas atmosphere of the reaction mixture for a period of time of at least about 1 minute.

Nanocrystals of essentially any type and composition prepared by essentially any method can be modified using the methods described herein. Suitable examples of nanocrystals that can be modified according to the methods described herein include, but are not limited to, cadmium selenide, cadmium chalcogenide, lead chalcogenide, zinc chalcogenide, mercury chalcogenide, or oxides, phosphides, nitrides, or arsenides of gold, silver, cobalt, platinum, nickel, iron, or copper, and the like.

These and other objects and features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only illustrated embodiments of the invention and are therefore not to be considered limiting of its scope. The invention will be described and explained with additional specificity and detail through the use of the accompanying drawings in which.

DETAILED DESCRIPTION OF THE PREFERRED EMBODIMENTS

1. Introduction

The present disclosure describes methods in which the shape and/or size of previously synthesized colloidal nanocrystals can be modified. The methods described herein include simple, one-step procedures in which the shape of previously synthesized colloidal nanocrystals having a first size and shape can be selectively modified to produce nanocrystals having a second size and/or a second shape (see, e.g., FIG. 1). The methods rely on controlled reversal of the nanocrystal growth process via competing thermodynamic and kinetic processes, allowing one to predictably control the degree of nanocrystal shape and size-modification. The term "selectively modifying" nanocrystals or "selectively removing" atoms from nanocrystals to control shape or size does not include fracturing nanocrystals using mechanical force (e.g., milling or grinding) or non-specific chemical etching (e.g., mere acid or base etching).

The process enables fabrication of shape-modified nanocrystals with sizes and shapes in the quantum confinement regime, resulting in the three-dimensional confinement of created excitons within the nanocrystals. The nanocrystals therefore possess size- and shape-dependent electronic and optical properties, which makes them interesting candidates for applications in areas as diverse as electronics and photonics, solid-state lightning, energy, and health science. Furthermore, since the methods disclosed herein include simple one-step processes that can be conducted at modest temperatures and under moderate reaction conditions, high-throughput fabrication and integration into conventional commercial fabrication facilities can be readily achieved.

Figure 1:
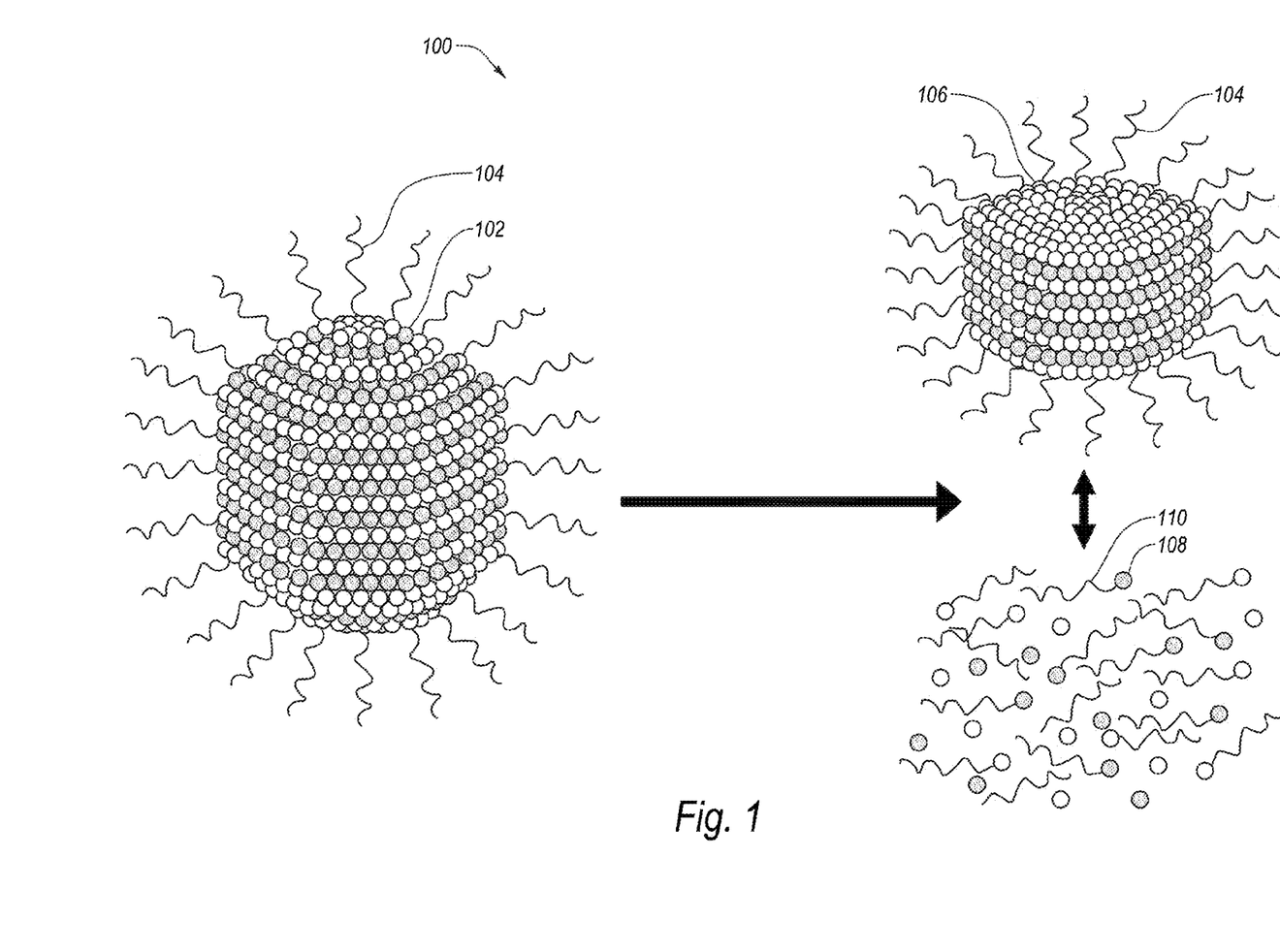
FIG. 1 depicts a schematic illustration of a method for selective shape modification of a nanocrystal, according to one embodiment of the present invention.

Referring now to FIG. 1, a schematic illustration of a process 100 for selective shape modification of a nanocrystal is depicted, according to one embodiment of the present invention. In the methods described herein, the reaction parameters (e.g., temperature, concentration of nanocrystals, concentration and type of ligands, and/or mixtures thereof, and reaction time) are adjusted to achieve the desired degree of shape modification. FIG. 1 illustrates a crystal 102 before shape modification, a crystal 106 after shape modification, and a number of ions 108 that are removed from the crystal in the modification reaction. Crystals 102 and 106 and ions 108 includes ligands 104 and 110 that are capable of binding to the surfaces of the crystals 102 and 106 and to the ions 108. According to the present disclosure, ligands 104 and 110 may be the same or different depending on the reaction parameters.

In the methods described herein, the reaction parameters (e.g., temperature, concentration of nanocrystals, concentration of ligands, type of ligands, reaction time, and/or mixtures thereof) are adjusted to achieve the desired degree of shape modification. The reaction parameter can be modified one at a time or in any combination in order to achieve the desired degree of shape modification.

For example, the temperature during modification is one important factor in determining conditions for the nanocrystal shape modification. The reaction temperature should be high enough to allow the solvents to overcome the bonding energy of the crystalline materials and to allow to allow for rearrangement and annealing of atoms while being low enough to allow some degree of kinetic and thermodynamic selectivity (e.g., it is desirable that the dissolution proceed at a reasonable rate without proceeding too quickly). In addition, because different crystal faces have different surface energies and therefore different bond strengths and reactivities of the atoms occupying these different faces, temperature is a parameter that can be used to exert control over removal of ions from selected crystal faces.

In one aspect, the temperature of the modification reaction may be in a range from about room-temperature (i.e., about 15-20° C.) to about 240° C. One will of course appreciate that the nanocrystal modification process will likely proceed quite slowly at temperatures as low as 15° C. Nonetheless, the modification reaction can proceed at low temperatures, although it may take several days to for detectable nanocrystal modification to occur at low temperature. Preferably, the lower end of the reaction temperature range should be at least about 35° C., at least about 45° C., at least about 50° C., at least about 60° C., at least about 70° C., at least about 80° C., at least about 90° C., or at least about 100° C. in order for the size and/or shape modification reaction to proceed at an appreciable rate.

Another important factor in nanocrystal modification is the concentration ratio in the reaction mixture of nanocrystals 102 and 106 to the concentration of ligands 104 and 110 that are capable of interacting with one or more crystalline components. The ligands 104 and 110 play two possible roles in the process of nanocrystal modification. In one role, the ligands 104 can bind to the surface of the nanocrystals 102 and 106, thus stabilizing the crystalline state of the nanocrystals 102 and 106 and affecting their dissolution rate by reducing the effective surface area of the crystals 102 and 106. In addition, because different faces of the nanocrystals 102 and 106 have different surface energies and therefore different bonding energies vis-à-vis the ligands 104, ligand concentration can be used to favor certain nanocrystal shapes (e.g., spheroids vs. rods vs. tetrapods). For example, if the bonding energies and concentration of ligand are such that a set of equivalent faces of the crystal are saturated with ligand while the other faces are open, dissolution from the open faces may be preferred resulting in the formation of rods. In another possibly concurrent role, the ligands 110 can bind to ions 108 in solution as they come off the nanocrystals 102 and 106, thus stabilizing the solution state of the ions 108 and affecting the equilibrium of the dissolution reaction.

The concentration of ionic crystalline components can be another important factor in the controlled dissolution process. For instance, as the crystals dissolve, the concentration of ions (e.g., Cd or Se ions) increases over time. The concentration of ions in solution can affect the equilibrium or end-point of the dissolution process because the reaction will reach equilibrium when the concentration of one or more ions reaches the saturation point. In one aspect, it was found that the equilibrium point could be shifted by "spiking" the dissolution mixture with one or more precursor materials (e.g., cadmium acetate). The inventors found that this "spiking" could be used to successfully shift the equilibrium of the modification reaction provided only one crystalline precursor (e.g., a Cd precursor or a Se precursor) was added to the reaction mixture. In contrast, the inventors found that spiking the reaction mixture with both crystalline precursors simultaneously (e.g., adding both Cd and Se precursors) mostly induced growth of new crystallites instead of just modification of old ones. This is most likely due to the significantly different chemical potential of the nanocrystals in solution and the freshly injected precursors.

The time of modification can be another important factor in the modification reaction. In one aspect, the reaction can be allowed to run for a period of time sufficient to reach equilibrium or the reaction can be stopped before equilibrium. The speed of the reaction and the time needed to reach equilibrium can be affected by temperature and the concentration of the reactants. As such, the lower time limit for the modification reaction at least partly dependent on the temperature and the other reaction parameters. As such, the modification reaction should be allowed to proceed for at least about 1 minute, 5 minutes, 10, minutes, 20 minutes, 30 minutes, 60 minutes, or any interval of time therebetween. Likewise, the upper time limit for the modification reaction at least partly dependent on the temperature and the other reaction parameters. The reaction can be allowed to proceed to equilibrium, or the reaction can be stopped prior to reaching equilibrium based on a selected reaction time (e.g., 3 hours) or the reaction can be stopped when the modified nanocrystals achieve the desired properties, as determined, for example, by a spectroscopic technique or TEM.

In the processes described herein, purified previously synthesized nanocrystals are immersed in a solvent (e.g., an inert, organic solvent) in the presence of surface-stabilizing ligands and are heated to temperatures of about 100° C. to about 240° C. (under constant stirring and inert gas atmosphere). The heating temperature is maintained at a given temperature for times between several minutes and several hours (depending on the desired degree of shape modification).

Figure 2A:
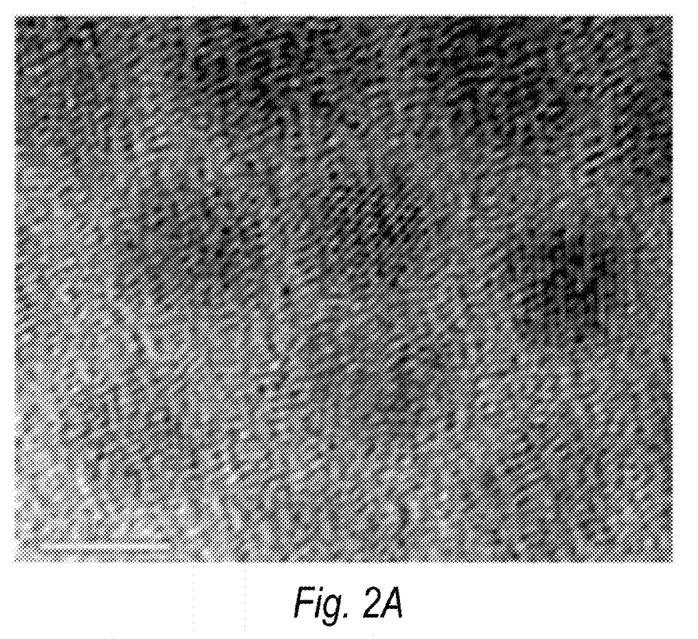
FIG. 2A is a transmission electron microscopy image illustrating CdSe nanocrystals prior to shape modification.
Figure 2B:
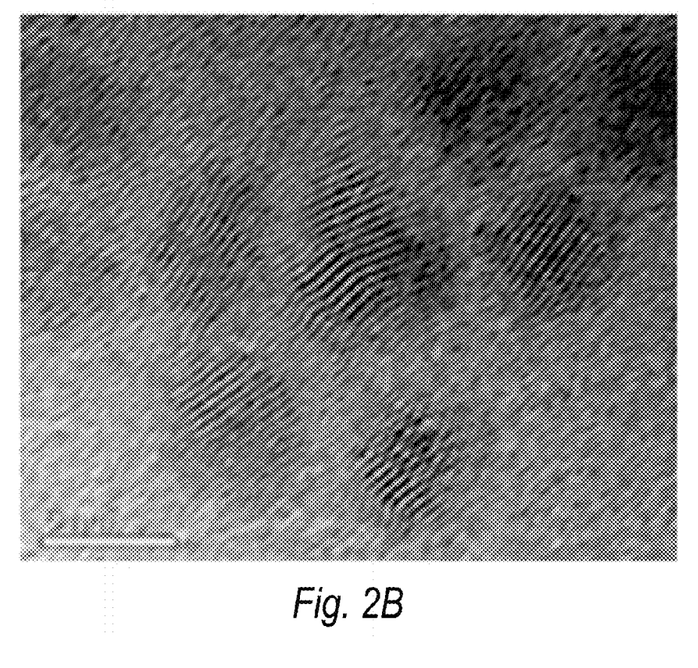
FIG. 2B illustrates is a transmission electron microscopy image illustrating CdSe nanocrystals after shape modification.

Shape modification can be monitored using a number of spectroscopic and microscopic techniques. For example, transmission electron microscopy (TEM) can be used to visually assess the degree and type of shape modification. FIGS. 2A and 2B illustrate nanocrystals before and after shape modification, according to embodiments of the present invention. As illustrated in FIG. 2A, as-synthesized CdSe nanocrystals display uniform shapes with well-defined uniform crystal faces (as expected for wurtzite-type CdSe nanocrystals) in TEM images. However, as illustrated in FIG. 2B, nanocrystals can show dramatically altered shapes after being subjected to the shape modification processes described herein. This is the direct result of non-uniform dissolution of ions from selected crystal faces. This is the direct result of non-uniform removal of ions from selected crystal faces, resulting in the step like crystal lattice features shown in FIG. 2B.

Figure 3:
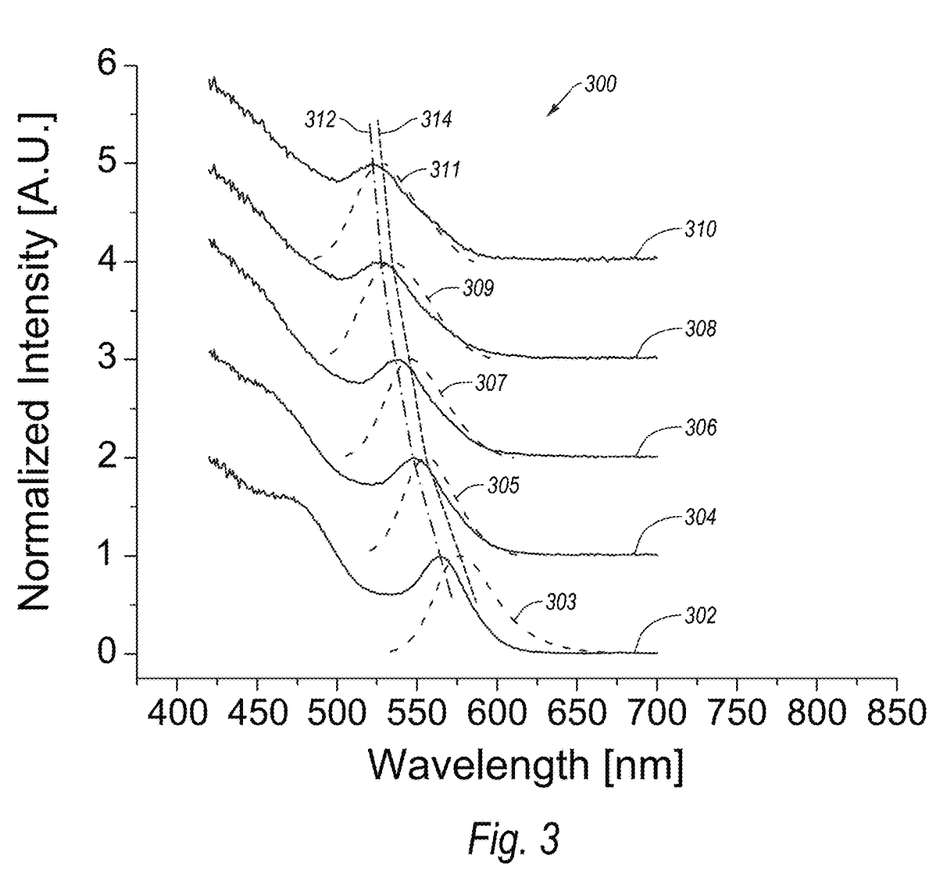
FIG. 3 illustrates UV-vis absorption and photoluminescence spectra of CdSe nanocrystals having increasing degrees of shape and/or size modification, according to one embodiment of the present invention.

Due to the quantum confinement effect in nanocrystals the degree of shape and size modification can also be monitored by UV-vis absorption and photoluminescence emission spectroscopy. An example is shown in FIG. 3, which illustrates the UV-vis absorption and photoluminescence emission spectra 300 of CdSe nanocrystals having various degrees of shape and/or size modification, according to the methods and procedures described herein.

The vertical progression represents the UV-vis absorption and photoluminescence emission properties of CdSe nanocrystals modified in different volumes of the solvent octadecene (spectra 304-311) as compared to the UV-vis absorption and photoluminescence emission properties of unmodified CdSe nanocrystals (spectra 302 and 303). Spectra 304 and 305, 306 and 307, 308 and 309, and 310 and 311 depict the properties of CdSe nanocrystals modified in 5 ml, 10 ml, 15 ml, and 20 ml of octadecene, respectively. Changing the volume of solvent affects the degree of modification because increasing the volume of solvent alters the concentration of the various reactants and products, which shifts the equilibrium of the reaction towards greater degrees of shape and/or size modification.

As the degree of modification increases (shown in the vertical progression from spectra 302 and 303 to spectra 310 and 311), there is a steady blue shift in the absorbance and emission spectra of the crystals. The blue shift in the absorbance and emission spectra can be seen in the blue shift in lines 312 and 314, which, respectively, transect the peaks in the absorbance and emission spectra.

Nanocrystals that are shape modified using the process disclosed herein retain their excellent photoluminescence emission properties and the process is highly tunable as a function of reaction parameters (temperature, reaction component concentrations, etc.). The tunability combined with the retention of the emission properties emphasize the great potential of the invented post-synthesis shape modification procedure for the predictable and controlled fabrication of a multitude of novel crystal-face selective shaped nanocrystals with strongly modified electronic and optical properties.

2. Methods for Nanocrystal Modification

The methods disclosed herein describe solution-based processes that can be used to precisely and predictably modify the shape of previously synthesized colloidal nanocrystals. The methods rely on the solubility behavior of crystalline materials to provide for controlled reversal of the nanocrystal growth process (i.e., dissolution). The methods disclosed herein are an equilibrium-controlled process that enables one to predictably tune the degree of nanocrystal dissolution. Moreover, since nanocrystals possess well-defined lattices and surface crystal faces with different surface energies and therefore different bond strengths and reactivities of the ions occupying these different faces, the invented process can be controlled to allow selective removal of ions from different crystal faces of the nanocrystals. This crystal face selective dissolution is induced by adjusting the reaction parameters (e.g., temperature, concentration of nanocrystals, concentration and type of ligands, and reaction time, and/or mixtures thereof).

In one embodiment, a method for post-synthesis modification of colloidal nanocrystals is disclosed. The method may include steps of (1) providing a first nanocrystal having a first size and a first shape, (2) forming a reaction mixture that includes the nanocrystal, at least one ligand capable of binding to at least one component of the nanocrystal, at least one solvent, and an inert gas atmosphere, and (3) modifying the size and/or shape of the nanocrystal in the reaction mixture for a period of time between about 1 minute and about 12 hours at a temperature in a range from about 100° C. to about 240° C. so as to produce at least a second nanocrystal having a second size and/or a second shape.

Suitable examples of nanocrystals that can be modified using the above described method include, but are not limited to, cadmium selenide, cadmium chalcogenide, lead chalcogenide, zinc chalcogenide, mercury chalcogenide, or oxides, phosphides, nitrides, or arsenides of gold, silver, cobalt, platinum, nickel, iron, or copper, and combinations thereof. Chalcogens are group 16 elements of the periodic table of the elements (i.e., O, S, Se, Te, and Po), although the term is typically reserved for sulfur, selenium, and tellurium. The chalcogenides referred to herein (i.e., cadmium chalcogenide, lead chalcogenide, zinc chalcogenide, and mercury chalcogenide) can be any one of or a mixture of sulfides, selenides, and tellurides.

In one embodiment the first shape of the nanocrystal is substantially spheroidal. Nanocrystals having other starting shapes such as rods, fibers, and tetrapods can also be shape modified using the methods disclosed herein.

The shape modification process disclosed herein can be used to modify the shape and/or size of previously synthesized nanocrystals. As such, in one embodiment, the second size is smaller than the first size. In another embodiment, the second shape is different than the first shape. For example, the second shape can be at least one of spheroidal, rod-shaped, fiber-shaped, or tetrapod-shaped.

In one embodiment, the at least one solvent can include an inert, organic solvent. Suitable examples of inert, organic solvents include, but are not limited to alkanes, alkenes, phenyl ethers, chloro alkanes, fluoro alkanes, toluene, or squalane. Preferably, at least one solvent has a boiling point in a range from about 80° C. to about 350° C. More preferably, the inert solvent has a boiling point in a range from about 100° C. to about 300° C., or most preferably, the inert solvent has a boiling point in a range from about 110° C. to about 280° C.

Examples of suitable ligands that can interact with one or more components of the crystal and that can be included in the reaction mixture include alkyl carboxylic acids, alkyl amines, alkyl phosphines, alkyl phosphonic acids, or alkyl sulfides, and combinations thereof. Preferably, the ligand has an aliphatic chain that includes at least four carbon atoms.

Suitable examples of inert gases that can be used to provide an inert gas atmosphere (i.e., a non-reactive, moisture-free atmosphere) include, but are not limited to, argon, nitrogen, helium, and the like.

When the nanocrystal in the modification reaction reaches its desired size (as determined by reaction time or one or more monitoring techniques), the modification of the nanocrystal can be stopped or at least significantly slowed by cooling the reaction mixture to ambient temperature.

Once the reaction has been stopped or slowed, the nanocrystal can be purified from the reaction mixture. An exemplary purification method includes (1) extracting the nanocrystal from the reaction mixture using at least one solvent that is immiscible in the reaction mixture, (2) precipitating the nanocrystal out of the extraction solvent and separating the precipitated nanocrystal from the extraction solvent by centrifugation, (3) suspending the nanocrystal in a fresh solvent. Appropriate fresh solvents include, but are not limited to, hexanes, toluene, and/or chloroform. The purified and resuspended nanocrystals can be characterized and/or used in a variety of experiment or techniques.

In another embodiment, a method for size and/or shape modification of colloidal nanocrystals is disclosed. The method includes (1) providing nanocrystals having a first size and a first shape, (2) modifying the size and/or shape of the nanocrystals in a reaction mixture under an inert-gas atmosphere at a temperature in a range from about 100° C. to about 240° C., wherein the reaction mixture includes the nanocrystals, at least one solvent, and at least one ligand, (3) monitoring the modification of the nanocrystals in the reaction mixture using at least one of UV-vis absorption spectroscopy, photoluminescence emission spectroscopy, and/or transmission electron microscopy, and (4) stopping the modification and purifying the nanocrystals from the reaction mixture when the nanocrystals achieve a selected second size and/or a second shape.

Nanocrystals of essentially any type and composition prepared by essentially any method can be modified using the method described above. Suitable examples of nanocrystals that can be modified according to the methods described herein include, but are not limited to, cadmium selenide, cadmium chalcogenide, lead chalcogenide, zinc chalcogenide, mercury chalcogenide, or oxides, phosphides, nitrides, or arsenides of gold, silver, cobalt, platinum, nickel, iron, or copper, and the like.

Nanocrystals of essentially any shape or size can be modified using the methods described herein. In one example, the nanocrystals have a first size of less than about 100 nm in one or more crystalline dimensions, or less than about 50 nm in one or more crystalline dimensions, less than about 30 nm in one or more crystalline dimensions, or less than about 10 nm in one or more crystalline dimensions.

In one aspect of the method, the first shape is substantially spheroidal. In another aspect, the nanocrystals have a first size and shape that is substantially monodisperse. A collection of objects are said to be monodisperse if they have the same size and shape. In one aspect, the nanocrystals are substantially monodisperse both before and after shape modification.

In one aspect of the method, the nanocrystals are smaller after modification (i.e., the second size is smaller than the first size). In one example, the nanocrystals have a second size of less than about 100 nm in one or more crystalline dimensions, or less than about 50 nm in one or more crystalline dimensions, less than about 30 nm in one or more crystalline dimensions, or less than about 10 nm in one or more crystalline dimensions. In one aspect, the second shape is different than the first shape.

In yet another embodiment, a method for post-synthesis modification of colloidal nanocrystals includes (1) providing a plurality of nanocrystals having a first size and a first shape, (2) forming a reaction mixture that includes the plurality of nanocrystals, at least one inert solvent, and at least one ligand, wherein the nanocrystals and the ligand are added in a molar ratio that ranges from about 1:1 to about $1:1 \cdot 10^{10}$, (3) conditioning the reaction mixture by first stirring under vacuum at ambient temperature and second by stirring under a vacuum at a temperature in a range from about 50° C. to about 100° C., (4) adding an inert-gas atmosphere to the reaction mixture and heating the reaction mixture to a temperature in a range from about 100° C. to about 300° C., and (5) selectively dissolving the nanocrystals such that the nanocrystals are modified so as to have a second size and shape, wherein the selective dissolving includes maintaining the temperature, stirring, and the inert gas atmosphere of the reaction mixture for a period of time between about 1 minute and about 12 hours.

In one embodiment, selectively dissolving the nanocrystals includes modifying at least one of the temperature, the molar ratio of the nanocrystals to the ligands, or the concentration of nanocrystals and/or ligands in the reaction such that dissolution of the nanocrystals is preferred from one or more faces of the crystal.

As such, the method can preferably include adding the nanocrystals and the ligand or ligand mixtures in a molar ratio that ranges from about 1:2 to about $1:1 \cdot 10^{8}$. More preferably, the method can preferably include adding the nanocrystals and the ligand in a molar ratio that ranges from about 1:5 to about $1:1 \cdot 10^{5}$. In another aspect, the method can further include selectively dissolving the nanocrystals at a temperature in a range from about 125° C. to about 275° C., or at a temperature in a range from about 150° C. to about 240° C. One will appreciate of course, that the molar ratio of nanocrystals to ligands and temperature are interacting parameters and that reaction conditions can include modifying the parameters one at a time or in combination.

3. Examples

Methods described herein can be used to for the modification (i.e., shape and or size modification) of colloidal nanocrystals via a selective dissolution route at a temperature between about 100° C. and about 240° C. under an inert atmosphere. The modification typically starts with immersing previously synthesized nanocrystals in a solvent in the presence of a ligand that is capable of binding to or interacting with one or more components of the nanocrystals. For instance, the ligands can selectively interact with atoms on one or more faces of the crystal or with ions removed from the crystals. The reaction mixture is stirred at a given temperature for several seconds to several days, depending on the desired end-size of the nanocrystals and the chosen reaction temperature.

When the desired size of the nanocrystals is reached, as monitored, for example, by time, spectroscopic properties, or size observed in a transmission electron microscope, the reaction is stopped by cooling the reaction mixture to room temperature and separating the modified nanocrystals from the modification mixture (solvent, ions, and ligands) An exemplary purification method includes (1) extracting the nanocrystals from the reaction mixture using at least one solvent that is immiscible in the reaction mixture, (2) precipitating the nanocrystals out of the extraction solvent and separating the precipitated nanocrystals from the extraction solvent by centrifugation, (3) suspending the nanocrystals in a fresh solvent. Appropriate fresh solvents include, but are not limited to, hexanes, toluene, and/or chloroform. Purified and re-dissolved nanocrystals are used for structural (transmission electron microscopy) and optical (UV-vis absorption and photoluminescence spectroscopy) characterization studies.

Example 1

Modification of Cadmium Selenide Nanocrystals

One example includes the shape and/or size modification of colloidal cadmium selenide nanocrystal quantum dots by a crystal face selective growth reversal (dissolution) procedure. For the shape modification process a round flask is filled with 0.5 g octadecylamine, appropriate amounts of CdSe nanocrystal quantum dots dissolved in hexanes ($1:1$-$5 \times 10^5$ molar ratio of nanocrystals:octadecylamine) and 5-20 mL octadecene and sealed. This mixture is first stirred at room temperature under vacuum for 30 minutes and then heated to 100° C. to ensure the removal of solvents and dissolved gases. The atmosphere is then switched from vacuum to argon gas and the solution is held at 100-240° C. for times between a few minutes and several hours (depending on the desired degree of shape modification). The growth-reversal (dissolution) progress is monitored by taking aliquots from the reaction mixture at given time intervals for optical spectroscopy measurements and transmission electron microscopy imaging. When the desired shape modification of the CdSe nanocrystal quantum dots is reached, the process is stopped by cooling the reaction mixture to room temperature.

When amine ligands are used, the purification procedure is as follows. The CdSe nanocrystals are separated from the reaction mixture by first adding 10 mL of hexanes and 20 mL methanol to the reaction mixture. This results in the formation of two liquid layers with the nanocrystals dissolved in the upper hexanes layer, which is extracted. This is followed by the addition of 15 mL acetone to the extracted nanocrystal solution. Under this condition, the nanocrystals precipitate out of the reaction solution and can be separated from it by centrifugation. The separated and purified nanocrystals are then re-dissolved in appropriate amounts of solvent (such as hexane, toluene, or chloroform) and characterized.

When carboxylic acid ligands are used, the purification procedure is as follows. The size-modified CdSe nanocrystals are separated from the reaction mixture by first adding 10 mL of hexanes to the reaction mixture followed by 20 mL of ethanol. Under these conditions the nanocrystals precipitate out of the solution and can be separated from the reaction solution by centrifugation. The separated and purified nanocrystals are then washed with acetone and re-dissolved in appropriate amounts of solvent (such as hexane, toluene, or chloroform).

Example 2

Modification of Lead Selenide Nanocrystals

Another example of the claim is to post-synthetically modify the shape of colloidal lead selenide (PbSe) nanocrystal quantum dots by a crystal face selective growth reversal (dissolution) procedure. For the shape modification process a round flask is filled with 0.3 mL oleic acid, appropriate amounts of PbSe nanocrystal quantum dots dissolved in tetrachloroethylene solvent ($1:1-5\times10^5$ mole ratio of nanocrystals:oleic acid) and additional 5-20 mL tetrachloroethylene and sealed. This mixture is first stirred at room temperature under vacuum for 2-5 minutes. The atmosphere is then switched from vacuum to argon gas and the solution is held at 50-75° C. for times between a few minutes and several hours (depending on the desired degree of shape modification). The growth-reversal (dissolution) progress is monitored by taking aliquots from the reaction mixture at given time intervals for optical spectroscopy measurements and transmission electron microscopy imaging. When the desired shape modification of the PbSe nanocrystal quantum dots is reached, the process is stopped by cooling the reaction mixture to room temperature.

The purification procedure is as follows. The size-modified PbSe nanocrystals are separated from the reaction mixture by first adding 10 mL of hexanes to the reaction mixture followed by 20 mL of ethanol. Under these conditions the nanocrystals precipitate out of the solution and can be separated from the growth solution by centrifugation. The separated and purified nanocrystals are then washed with acetone and re-dissolved in appropriate amounts of solvent (such as hexane, toluene, tetrachloroethylene, or chloroform).

Example 3

Shape Modification of Other Nanocrystal Types

The invented post-synthesis nanocrystal shape modification process can be applied to nanocrystals other than cadmium selenide and lead selenide, including, but not restricted to cadmium chalcogenide, lead chalcogenide, zinc chalcogenide, and mercury chalcogenide nanocrystals; other types of nanocrystals such as oxides, phosphides, nitrides, and arsenides; metals such as gold, silver, cobalt, platinum, nickel, iron, and copper.

Other type of surface-stabilizing ligands can be used for the invented crystal face selective growth reversal (dissolution) process, including, but not restricted to alkyl carboxylic acids, alkyl amines, alkyl phosphines, and alkyl sulfides.

The reaction solvent is not restricted to octadecene or tetrachloroethylene, but other solvents can be used (depending on the chosen reaction temperature), including, but not restricted to alkanes, alkenes, phenyl ethers, toluene, squalane, and chloro and fluoro alkanes.

The invented growth reversal (dissolution) process can be tuned to either remove ions from selected crystal faces (shape modification) or uniformly remove ions from the entire nanocrystal surface (size modification).

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:
1. A method for nanocrystal modification, comprising:
providing purified previously synthesized nanocrystal quantum dots which exhibit three-dimensional confinement of created excitons within the nanocrystal quantum dots, the previously synthesized nanocrystal quantum dots comprising at least one of cadmium selenide, cadmium chalcogenide, lead chalcogenide, zinc chalcogenide, or mercury chalcogenide, wherein the previously synthesized nanocrystal quantum dots have a first size and a first shape and have been previously synthetically produced and purified by separating the previously synthesized nanocrystal quantum dots from a reaction mixture in which they were synthesized;
adding the purified previously synthesized nanocrystal quantum dots to an inert reaction solvent and at least one ligand to form a reaction mixture so that the reaction mixture includes the previously synthesized nanocrystal quantum dots, the inert reaction solvent, an inert gas atmosphere, and the at least one ligand capable of binding to atoms on at least one crystalline face of the previously synthesized nanocrystal quantum dots and capable of binding to atoms in solution removed from the previously synthesized nanocrystal quantum dots;
selecting reaction conditions for the reaction mixture that cause the atoms to be removed from the previously synthesized nanocrystal quantum dots, wherein the reaction conditions include selecting a nanocrystal to ligand molar ratio that ranges from about 1:1 to about $1:1\cdot10^{10}$ and a reaction temperature in a range from 50° C. to about 240° C.;
changing the shape of the previously synthesized nanocrystal quantum dots in the reaction mixture by selectively removing atoms from one or more crystalline faces of the previously synthesized nanocrystal quantum dots for a period of time of at least about 1 minute under the reaction conditions to produce nanocrystals that have a different shape compared to the previously synthesized nanocrystal quantum dots, wherein the first shape is spheroidal and the nanocrystals having a changed shape are least one of rod-shaped, fiber-shaped, or tetrapod-shaped;

wherein the molar ratio of ligand to nanocrystals controls a rate or extent of nanocrystal dissolution and the shape of the nanocrystals obtained, and wherein the nanocrystals having a changed shape, have a size and shape in a quantum confinement regime, resulting in three-dimensional confinement of created excitons within the nanocrystals.

2. The method of claim 1, the at least one solvent including at least one of an alkane, an alkene, a phenyl ether, a chloro alkane, a fluoro alkane, toluene, or squalene, the at least one solvent having a boiling point in a range from about 80° C. to about 350° C.

3. The method of claim 2, the at least one solvent having a boiling point in a range from about 100° C. to about 300° C.

4. The method of claim 2, the at least one solvent having a boiling point in a range from about 110° C. to about 280° C.

5. The method of claim 1, the ligand including at least one of an alkyl carboxylic acid, an alkyl amine, an alkyl phosphine, an alkyl phosphonic acid, or an alkyl sulfide, the ligand having an aliphatic chain that includes at least four carbon atoms.

6. The method of claim 1, wherein the inert gas comprises at least one of argon, nitrogen, or helium.

7. The method of claim 1, further comprising stopping the modification of the nanocrystals by cooling the reaction mixture to ambient temperature.

8. The method of claim 7, further comprising purifying the nanocrystals having a changed shape from the reaction mixture, the purifying including:
extracting the nanocrystals from the reaction mixture using at least one solvent that is immiscible in the reaction mixture;
precipitating the nanocrystals out of the extraction solvent and separating the precipitated nanocrystals from the extraction solvent by centrifugation; and
suspending the nanocrystals in a fresh solvent.

9. The method of claim 1, wherein the step of changing the shape of the previously synthesized nanocrystal quantum dots is performed in a different vessel than the previously synthesized nanocrystal quantum dots were synthesized in.

10. The method of claim 1, wherein the nanocrystals having a changed shape which are least one of rod-shaped, fiber-shaped, or tetrapod-shaped comprise platelets.

11. A method for changing the size and shape of colloidal nanocrystals, comprising:
providing previously synthesized nanocrystals, the previously synthesized nanocrystals being provided as a suspension consisting of the previously synthesized nanocrystals in an inert solvent, the nanocrystals comprising at least one of cadmium selenide, cadmium chalcogenide, lead chalcogenide, zinc chalcogenide, or mercury chalcogenide, wherein the nanocrystals have a first size and a first shape and have been previously synthetically produced;
wherein the inert solvent includes at least one of an alkane, an alkene, a phenyl ether, a chloro alkane, a fluoro alkane, toluene, or squalene and has a boiling point in a range from about 100° C. to about 300° C.;
selecting reaction conditions for a reaction mixture that cause atoms to be removed from the previously synthesized nanocrystals, wherein the reaction conditions include selecting an inert gas atmosphere, a nanocrystal to ligand molar ratio that ranges from about 1:1 to about $1:1 \cdot 10^{10}$, and a reaction temperature in a range from 50° C. to about 240° C.;
forming the reaction mixture by adding the suspension of previously synthesized nanocrystals to the ligand;
reducing the size and changing the shape of the previously synthesized nanocrystals in the reaction mixture by selectively removing atoms from one or more crystalline faces of the previously synthesized nanocrystals under the reaction conditions;
monitoring the size change and shape change of the nanocrystals in the reaction mixture using at least one of UV-vis absorption spectroscopy, photoluminescence emission spectroscopy, or transmission electron microscopy;
stopping the reaction and purifying the nanocrystals from the reaction mixture when the nanocrystals achieve a selected second size and shape,
wherein the molar ratio of ligand to nanocrystals controls, at least in part, a rate or extent of nanocrystal dissolution and the shape of the nanocrystals obtained, and
wherein the selected second size and shape results in a quantum confinement regime with three-dimensional confinement of created excitons within the nanocrystals, and blue shifted absorbance and emission spectra of the nanocrystals having the selected second size and shape.

12. The method of claim 11, wherein the first shape is substantially spheroidal.

13. The method of claim 11, wherein the second size is less than about 100 nm in one or more crystalline dimensions.

14. The method of claim 11, the inert solvent having a boiling point in a range from about 110° C. to about 280° C.

15. The method of claim 11, the ligand including at least one of an alkyl carboxylic acid, an alkyl amine, an alkyl phosphine, an alkyl phosphonic acid, or an alkyl sulfide, the ligand having an aliphatic chain that includes at least four carbon atoms.

16. The method of claim 11, wherein the inert gas comprises at least one of argon, nitrogen, or helium.

17. The method of claim 11, further comprising stopping changing the size and shape of the nanocrystals by cooling the reaction mixture to ambient temperature.

18. The method of claim 17, further comprising purifying the nanocrystals from the reaction mixture, the purifying including:
extracting the nanocrystals from the reaction mixture using at least one solvent that is immiscible in the reaction mixture;
precipitating the nanocrystals out of the extraction solvent and separating the precipitated nanocrystals from the extraction solvent by centrifugation; and
suspending the nanocrystals in a fresh solvent.

19. The method of claim 11, wherein forming the reaction mixture further comprises adding an inert reaction solvent that is different from the inert solvent in which the previously synthesized nanocrystals are suspended.

20. A method for nanocrystal modification, comprising:
providing purified previously synthesized nanocrystal quantum dots which exhibit three-dimensional confinement of created excitons within the nanocrystal quantum dots, the previously synthesized nanocrystal quantum dots comprising at least one of cadmium selenide, cadmium chalcogenide, lead chalcogenide, zinc chalcogenide, or mercury chalcogenide, wherein the previously synthesized nanocrystal quantum dots have a first size and a first shape and have been previously synthetically produced and purified by separating the previously synthesized nanocrystal quantum dots from a reaction mixture in which they were synthesized;

adding the purified previously synthesized nanocrystal quantum dots to an inert reaction solvent and at least one ligand to form a reaction mixture so that the reaction mixture includes the previously synthesized nanocrystal quantum dots, the inert reaction solvent, an inert gas atmosphere, and the at least one ligand capable of binding to atoms on at least one crystalline face of the previously synthesized nanocrystal quantum dots and capable of binding to atoms in solution removed from the previously synthesized nanocrystal quantum dots;

the at least one solvent including at least one of an alkane, an alkene, a phenyl ether, a chloro alkane, a fluoro alkane, toluene, or squalene, the at least one solvent having a boiling point in a range from about 100° C. to about 300° C.;

selecting reaction conditions for the reaction mixture that cause the atoms to be removed from the previously synthesized nanocrystal quantum dots, wherein the reaction conditions include selecting a nanocrystal to ligand molar ratio that ranges from about 1:1 to about $1:1 \cdot 10^{10}$ and a reaction temperature in a range from 50° C. to about 240° C.;

changing the shape of the previously synthesized nanocrystal quantum dots in the reaction mixture by selectively removing atoms from one or more crystalline faces of the previously synthesized nanocrystal quantum dots for a period of time of at least about 1 minute under the reaction conditions to produce nanocrystals that have a different shape compared to the previously synthesized nanocrystal quantum dots;

wherein the molar ratio of ligand to nanocrystals controls a rate or extent of nanocrystal dissolution and the shape of the nanocrystals obtained, and wherein the nanocrystals having a changed shape, have a size and shape in a quantum confinement regime, resulting in three-dimensional confinement of created excitons within the nanocrystals.

* * * * *